United States Patent
Zhang et al.

(10) Patent No.: US 8,656,921 B2
(45) Date of Patent: Feb. 25, 2014

(54) ADJUSTABLE SUPPORT FOR SOFT PALATE AND IMPLANTING METHOD THEREOF

(75) Inventors: Xiangmin Zhang, Guangzhou (CN); Xing Zhou, Guangzhou (CN)

(73) Assignees: Xiangmin Zhang, Guangzhou (CN); Xing Zhou, Guangzhou (CN)

( * ) Notice: Subject to any disclaimer, the term of this patent is extended or adjusted under 35 U.S.C. 154(b) by 179 days.

(21) Appl. No.: 13/129,383

(22) PCT Filed: Nov. 16, 2009

(86) PCT No.: PCT/CN2009/074959
§ 371 (c)(1),
(2), (4) Date: May 13, 2011

(87) PCT Pub. No.: WO2010/054603
PCT Pub. Date: May 20, 2010

(65) Prior Publication Data
US 2011/0214678 A1    Sep. 8, 2011

(30) Foreign Application Priority Data

Nov. 17, 2008  (CN) .......................... 2008 1 0219169
Sep. 27, 2009  (CN) .......................... 2009 1 0192688

(51) Int. Cl.
*A61F 5/56*    (2006.01)
*A61C 5/14*    (2006.01)

(52) U.S. Cl.
USPC .......................................... 128/848; 128/859

(58) Field of Classification Search
USPC .................... 128/848, 859–862; 433/6–7
See application file for complete search history.

(56) References Cited

U.S. PATENT DOCUMENTS 6,955,172 B2 * 10/2005 Nelson et al. ................ 128/848
2007/0256693 A1 * 11/2007 Paraschac et al. ........... 128/848

FOREIGN PATENT DOCUMENTS

| CN | 2010058137 Y | 1/2008 | ........... A61F 2/82 |
| JP | 2004-154583 A | 6/2004 | |
| JP | 2006-507038 T | 3/2006 | |
| JP | 2008-513163 T | 5/2008 | |
| WO | WO 2006/034434 A2 | 3/2006 | ........... A61F 5/56 |
| WO | WO 2008/060317 A2 | 5/2008 | ........... A61F 5/56 |

OTHER PUBLICATIONS

International Search Report, PCT/CN2009/074959, Dec. 31, 2009, 6 pages.
Zhang, Notice of Reasons for Rejection, JP 2011-535863, Jul. 18, 2013, 4 pgs.

* cited by examiner

*Primary Examiner* — Patricia Bianco
*Assistant Examiner* — Ophelia A Hawthorne
(74) *Attorney, Agent, or Firm* — Morgan, Lewis & Bockius LLP

(57) ABSTRACT

The current invention provides an adjustable soft palate support and an implantation method. The adjustable soft palate support is a flat implant including a hard palate connecting end and a support. The support is a flat implant connected to the hard palate connecting end and is inserted into the soft palate. The hard palate connecting end is connected to the hard palate and includes a connecting structure and an adjustment mechanism. The connecting structure is configured to affix the support to the hard palate, and the adjustment mechanism is configured to control the movement or the curvature of the support or the lifting degree of the soft palate. The adjustment mechanism may be set to be in an on state to reduce interference with swallowing or to an off state to enlarge an airway during breathing, thereby treating snoring and obstructive sleep apnea/hypopnea syndrome (OSAHS).

10 Claims, 14 Drawing Sheets

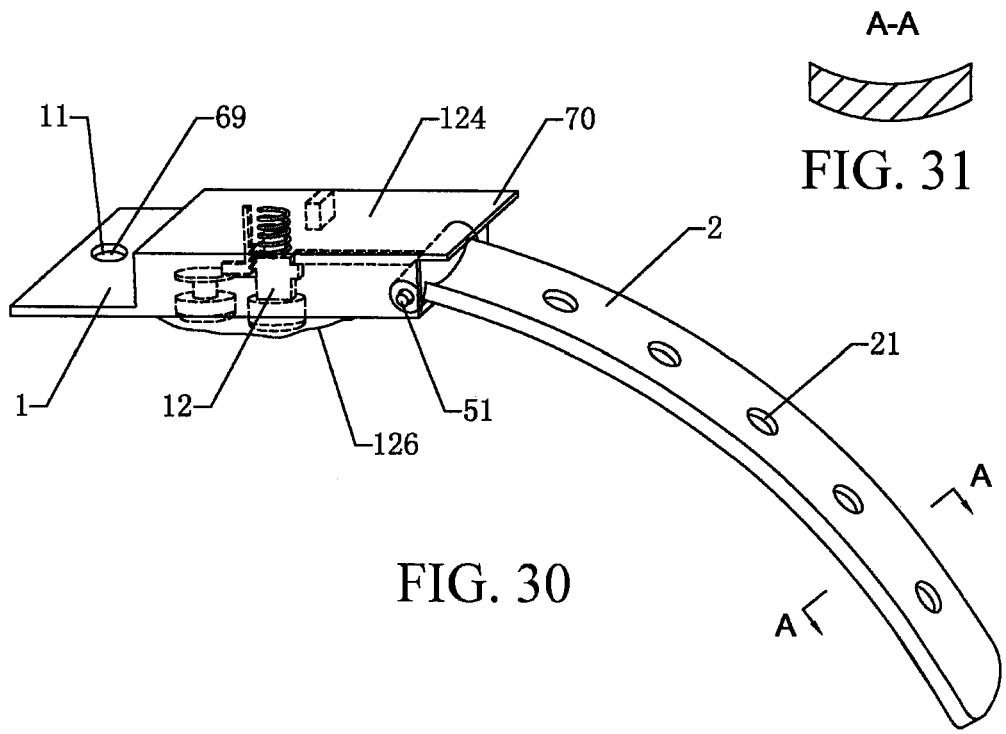
FIG. 30
FIG. 31
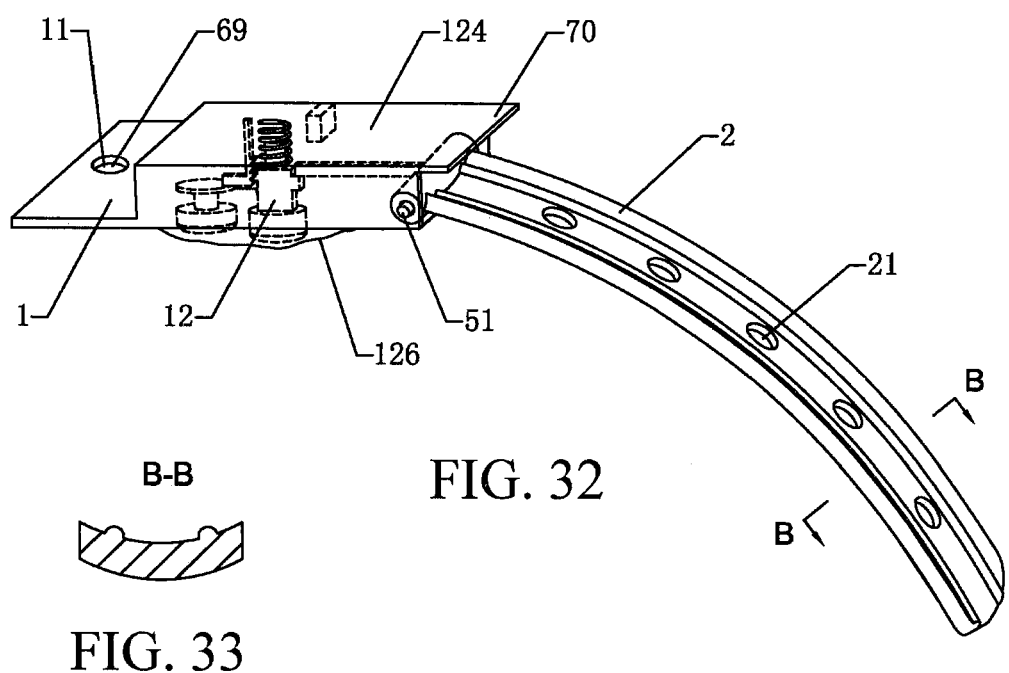
FIG. 32
FIG. 33

ADJUSTABLE SUPPORT FOR SOFT PALATE AND IMPLANTING METHOD THEREOF

CROSS REFERENCE TO RELATED APPLICATIONS

This Application is a United States National Stage Application filed under 35 U.S.C. §371 of PCT Patent Application Serial No. PCT/CN2009/074959 filed on Nov. 16, 2009 which claims benefit of and priority to Chinese Patent Application Serial No. 200910192688.7 filed on Sep. 27, 2009, and Chinese Patent Application Serial No. 200810219169.0 filed on Nov. 17, 2008, the disclosures of all of which are hereby incorporated by reference in their entirety.

BACKGROUND OF THE INVENTION

1. Field of the Invention

The present invention relates to an adjustable soft palate support, and more particularly to an adjustable soft palate support and an implantation method for treating adult obstructive sleep apnea/hypopnea syndrome (OSAHS) and snoring.

2. Related Art

Adult OSAHS is a sleep breathing disorder with clinical features of snoring and apnea caused by upper airway collapse and obstruction during sleep. The morbidity of OSAHS is about 4% among adult men and about 2% among adult women even according to the lowest diagnosis criteria, and OSAHS presents a serious threat to the life and health of patients.

As for the pathogenesis of OSAHS, it is generally considered that the main cause is that, pharyngeal muscles for maintaining the upper airway open relax during sleep, resulting in soft tissue collapse and obstruction, and the plane of obstruction is usually located in the soft palate, tonsil, and tongue root. Many methods for treating OSAHS exist, which include two types, that is, non-surgical treatment and surgical treatment.

Methods of Non-Surgical Treatment Mainly Include:

1. Continuous Positive Airway Pressure (CPAP), in which a breathing machine capable of continuously generating a positive pressure is closely connected to the nose and face of a patient via a nasal mask, so as to prevent collapse and obstruction of the soft tissues of the airway during sleep. Though the method has a good effect, it is difficult for approximately ⅔ of the patients to adapt to the machine, and they cannot sleep when wearing the machine.

2. Oral appliance. A device is placed in a mouth to move forward the mandible or pull forward the tongue, so as to enlarge the pharyngeal cavity and release the airway obstruction during sleep. The method has many types and produces a certain effect, but most patients cannot adapt to it. The oral appliance leads to irritation and foreign body sensation, causing that the user cannot fall asleep, and may have temporomandibular joint injury with long term use.

International Application PCT/US2005/00139 has disclosed a method and a device for relieving upper airway obstructions. The device includes a mouthpiece that is adapted to form a sealed cavity within a human mouth. The patient bites the device during sleep, so as to form the sealed cavity within the human mouth. A negative pressure generator is connected to the device, which pulls the patient's tongue and/or soft tissues of the upper airway up and away from the posterior pharyngeal wall to open the airway, so as to reduce the occurrence of OSAHS.

Chinese Utility Model Patent ZL200620110299.7 has disclosed a tongue forward-moving device for treating OSAHS and snoring. The tongue forward-moving device includes a semi-lunar base, in which a semi-lunar upper-tooth receiving groove formed by front and rear flanges is provided at an upper portion of the base; an arc-shaped rear baffle is provided at a bottom portion of the base, and a tongue anchoring hole running through front and rear edges is provided in the center of the base; and an arc-shaped front baffle is provided at the bottom portion of the base, and a bracket for a lower front dentition is formed between the front and rear baffles. The tongue forward-moving device provides a die for being actively bitten by a patient with upper and lower front dentitions, so that the upper and lower muscles are subconsciously in a relatively tension state during sleep, thereby forming a stable fulcrum between the maxilla and mandible and the tongue forward-moving device. The tongue anchoring hole provides a comfortable anchor station for the apex of tongue, and regulates the tongue between the tongue anchoring hole and the hyoid bone, so as to maintain a smooth airway at the mouth and pharynx, thereby achieving the objective of treating OSAHS and snoring.

Many patents similar to the device disclosed in International Application PCT/US2005/00139, Jan. 3, 2005, or the tongue forward-moving device disclosed in Chinese Utility Model Patent ZL200620110299.7 exist. All the patents use the teeth as a supporting point in the oral cavity, and various appliances are designed to change the tension state or position of the tongue or the soft palate during sleep, so as to achieve the objective of treating OSAHS and snoring. These appliances are placed in the oral cavity and are bitten and fixed before sleep, but since persons continuously change the posture and mouth shape during sleep, the appliances often cannot function effectively. In addition, it is uncomfortable and inconvenient for the patients to use the appliances.

Methods of Surgical Treatment Mainly Include:

1. Radiofrequency ablation, which is also referred to as low-temperature plasma radiofrequency ablation, and is a minimally invasive surgical method. An electrode is penetrated into the soft tissues which cause airway obstruction, such as the soft palate, tonsil, and tongue root, and is electrified to induce tissue coagulation, necrosis, fibrosis, and contraction by heating. The method has a certain therapeutic effect, is effective for a slight case, has a poor long-term efficacy, and is ineffective for serious patients.

2. Palatopharyngoplasty. Since Fujita improved the Palatopharyngoplasty of Ikematus, a Japanese scholar, into uvulopalatopharyngoplasty (UPPP) and introduced it to the US in 1981, various improved technologies based on UPPP, including Simmons method, Fairbanks method, Dickson method, Woodson method, Z-palatoplasty (ZPP), uvulopalatal flap (UPF), H-uvulopalatopharyngoplasty (H-UPPP) have been successively reported in literatures, which made a great contribution to symptom alleviation and recovery of OSAHS patients. Countless patients benefit from the surgical treatment solution. However, in terms of long-term effect, since the mucous membrane and soft palate tissue structure are excessively removed, functional muscles are injured, resulting in complications of nasal regurgitation during swallowing, rhinolalia aperta, and nasopharyngeal stenosis and atresia. It is the leading edge and focus for the research and development of OSAHS treatment technologies nowadays to develop a method and corresponding surgical instruments which create a smaller wound or perform surgical treatment in a minimally invasive manner.

3. Soft palate implantation. International Application PCT/US2002/007966, Mar. 14, 2002 has disclosed a braided palatal implant for snoring treatment. In the invention, the implant is embedded in the soft palate to alter the center of gravity of the soft palate when swinging with the air flow and alter the aerodynamic characteristics of the soft palate, so as to increase the critical air flow speed at the soft palate and the pharynx, thereby preventing snoring from occurring. However, the method fails to prevent OSAHS from occurring, for OSAHS occurs when the soft palate collapses and obstructs the upper airway, so that the method and the adopted implanted instrument cannot be used to treat OSAHS. For serious snoring patients, the risk of OSAHS is increased because the weight at the swinging portion of the soft palate is increased.

Based on the above, though generating a certain effect, the existing technologies and methods for treating OSAHS and snoring still have many defects, and have a poor long-term effect. Therefore, it is necessary to develop a new method and design a new instrument to treat OSAHS and snoring, in which the new method should create a wound as small as possible, and the new instrument should be safe, effective, simple, and reliable.

SUMMARY OF THE INVENTION

Research reports and clinical experience indicate that, the relaxation and collapse of the soft palate portion is the main cause of snoring and OSAHS.

In view of the cause of disease that snoring and OSAHS are caused by the relaxation and collapse of the soft palate portion, the concept of the present invention is: to design an implant with one end fixed to the hard palate and the other end implanted into the soft palate, so as to lift the relaxed and collapsed soft palate and a root portion of the tongue by using the hard palate as a supporting point. The central axis of the soft palate during natural swinging is changed by lifting the soft palate towards the tongue root, so as to enlarge the airway of the pharynx during breathing, thereby achieving the objectives of treating snoring and OSAHS. Since swallowing occurs frequently in a non-sleep state during the day, especially when eating, and snoring and OSAHS caused by the relaxation and collapse of the soft palate portion occur during sleep when swallowing occurs less frequently, an adjustable soft palate support is designed in the present invention, which is specifically as follows.

The adjustable soft palate support of the present invention is a flat implant made of a material capable of being implanted into a human body for a long term, including: a flat implant support capable of being inserted into a soft palate; and a hard palate connecting end that is configured to connect the support to a hard palate. The hard palate connecting end includes: a connecting structure, configured to fix the hard palate connecting end to the hard palate; and an adjustment mechanism, configured to control the movement or a curvature of the support or a lifting degree of the soft palate.

Further, the support has a radian matching a natural curvature when the soft palate of the human body relaxes.

The connecting structure on the hard palate connecting end includes at least one of a group of structures consisting of: a hole structure, a U-shaped clamp structure, a hook structure, a rivet-type structure, and a self-expanding lock structure.

The adjustment mechanism on the hard palate connecting end is a switch structure having an on state and an off state; when the adjustment mechanism is in the on state, the support implanted into the soft palate is capable of moving with natural swinging of the soft palate; and when the adjustment mechanism is in the off state, the support implanted into the soft palate is capable of lifting the soft palate and changing a central axis of the soft palate during natural swinging by lifting the soft palate towards a tongue root, so as to enlarge an airway of a pharynx during breathing.

Further, the switch structure of the adjustment mechanism at least includes the following structures: a single-key switch structure and a double-key switch structure.

The adjustment mechanism on the hard palate connecting end is a mechanism capable of adjusting the movement or the curvature of the support or the lifting degree of the soft palate through multiple distinct stages.

Further, the adjustment mechanism on the hard palate connecting end includes a multi-stage adjustment mechanism having one stage, two stages, or more than two stages.

The adjustment mechanism on the hard palate connecting end is a mechanism capable of continuously adjusting the movement or the curvature of the support or the lifting degree of the soft palate.

The adjustment mechanism on the hard palate connecting end includes a continuous adjustment mechanism for continuously adjusting a degree of lifting the soft palate by the support through rotary or linear movement.

Further, the hard palate connecting end further includes a housing, and the adjustment mechanism is mounted inside the housing.

The adjustment mechanism on the hard palate connecting end includes: an adjustment control key mounted on the housing, and the adjustment control key is covered by a flexible polymer material film capable of being implanted into the human body.

The housing includes the flexible polymer material film capable of being implanted into the human body, and the adjustment control key is covered by the flexible polymer material film.

The support is a flat object having zero or more holes.

Further, the support is selected from at least the following structures: a flat object having an arc-shaped cross section, a flat object having a corrugated cross section, and a flat object having reinforcing ribs.

The support includes at least one elastic module.

Further, the elastic module is a mechanism or an object deformable under an external force and shape-recoverable after the external force is removed.

The elastic module at least includes the following structures: an elastic polymer material sheet or strip or film, a spring structure, and a spring structure coated with a flexible polymer material.

The support includes at least one rigid module.

Further, the rigid module is a mechanism or an object that is configured to resist a predefined external force but deforms plastically if the external force is higher than a predefined level such that the rigid module cannot recover its original shape after the external force is removed.

The support is integrally or detachably connected to the hard palate connecting end.

The support is inserted into the soft palate by a length equal to $1/5$ to $4/5$, and most preferably, $2/3$ to $3/4$, of a total length of the soft palate.

The implantation method is to fix the hard palate connecting end to the hard palate, and insert the support into the soft palate.

With the adjustable soft palate support, since the hard palate connecting end is fixed to the hard palate, and the support is implanted into a muscular layer of the soft palate, the relaxed and collapsed soft palate and a part of the tongue root are lifted by using the hard palate as a supporting point. The central axis of the soft palate during natural swinging is changed by lifting the soft palate towards the tongue root, so as to enlarge the airway of the pharynx during breathing, thereby achieving the objectives of treating snoring and OSAHS. Since swallowing occurs frequently in a non-sleep state during the day, especially when eating, the adjustment mechanism may be adjusted to be in an on state, so that the support implanted into the soft palate can move with natural swinging of the soft palate, so as to reduce interference with swallowing; and before sleep, the adjustment mechanism may be adjusted to be in an off state, so that the support implanted into the soft palate can lift the soft palate. The central axis of the soft palate during natural swinging is changed by lifting the soft palate towards the tongue root, so as to enlarge the airway of the pharynx during breathing. Thereby, the occurrence of snoring and OSAHS is avoided.

Further, an adjustable soft palate support allowing for multi-stage adjustment and continuous adjustment is designed in the present invention. In this way, the support implanted into the soft palate may be adjusted to a suitable position by adjusting a control key implanted on the hard palate with a finger, an apex of tongue or a remote controller. Therefore, normal swallowing can be ensured in the non-sleep state, and the soft palate can be effectively lifted in the sleep state to maintain a smooth upper airway during sleep, thereby avoiding the occurrence of snoring and OSAHS.

The adjustable soft palate support of the present invention is skillfully designed, and a surgery may be performed under local anesthesia or general anesthesia. During the surgery, the adjustable soft palate supports of the present invention of different sizes are selected according to the severity of snoring and OSAHS. The surgery can be completed simply by making a small incision of 2 mm to 20 mm at the hard palate of the oral cavity, fixing the hard palate connecting end of the adjustable soft palate support of the present invention to the hard palate, inserting the support into the soft palate, and suturing the incision. Thus, the objective of minimally invasive treatment of snoring and OSAHS is realized. Clinical application has proved that, the method and implanted instrument of the present invention have the advantages of small wound, fast recovery, immediate effect, and reliable efficacy. Especially, the patient may conveniently adjust the degree of lifting the soft palate by the soft palate support according to his or her feeling after surgery, so as to achieve optimal treatment effect and comfort. Therefore, the method and implanted instrument of the present invention are popular with patients.

BRIEF DESCRIPTION OF THE DRAWINGS

FIG. 30 is a schematic structural view of an adjustable soft palate support of the present invention, in which in this embodiment, the cross section of the support 2 is arc-shaped, and the support 2 has good rigidity;

FIG. 31 is an A-A cross-sectional view of FIG. 30;

FIG. 32 is a schematic structural view of an adjustable soft palate support of the present invention, in which in this embodiment, a reinforcing rib is configured at the back of the support 2, two reinforcing ribs are configured at the cross section of the support 2, and the support 2 has good rigidity;

FIG. 33 is a B-B cross-sectional view of FIG. 32;

The meanings of the serial numbers in the above drawings are as follows:

"1" for a hard palate connecting end,
"2" for a support,
"11" for a connecting structure on the hard palate connecting end for fixing the support of the present invention to the hard palate,
"12" for an adjustment mechanism on the hard palate connecting end for controlling the movement or a curvature of the support or controlling a lifting degree of a soft palate,
"121" for a switch structure,
"122" for a multi-stage adjustment mechanism,
"123" for a continuous adjustment mechanism,
"124" for a housing of the adjustment mechanism,
"125" for an adjustment control key, and
"126" for a medical-purpose flexible material film;
"20" for an elastic module,
"21" for a through hole,
"22" for a convex-concave texture or rough surface,
"40" for a rigid module,
"50" for a pushrod,
"51" for a rotating shaft,
"52" for a position restoring spring,
"53" for a button close to incisors,
"54" for a button close to the tongue root,
"55" for a multi-stage positioning block,
"56" for a rotary adjustment switch,
"57" for a multi-stage adjustment positioning slot,
"58" for a positioning block,
"59" for a positioning slide block,
"60" for an adjustment rod,
"61" for an adjustment screw rod,
"62" for a guide rod,
"63" for an electrical device,
"64" for an electrical adjustment control switch,
"65" for a power supply,
"66" for a transmission mechanism,
"67" for a remote controller,
"68" for a circuit,
"69" for a fastening-screw through hole, and
"70" for a locking edge;
"101" for a hard palate,
"102" for a soft palate,
"103" for a nasopharynx,
"104" for a back end of the soft palate,
"105" for an epiglottis,
"106" for an esophagus,
"107" for a trachea,
"108" for a front end of the soft palate,
"109" for a supporting bone,
"110" for a nasal cavity,
"111" for an oral cavity,
"112" for a tongue,
"113" for a hard palate-soft palate junction,
"114" for a tongue root,
"115" for an adjustable soft palate support of the present invention, and
"116" for a fastener.

DETAILED DESCRIPTION OF THE INVENTION

In order to make the present invention more comprehensible, the pathogenesis of OSAHS is described with reference to FIG. 1 to FIG. 3.

Figure 1:
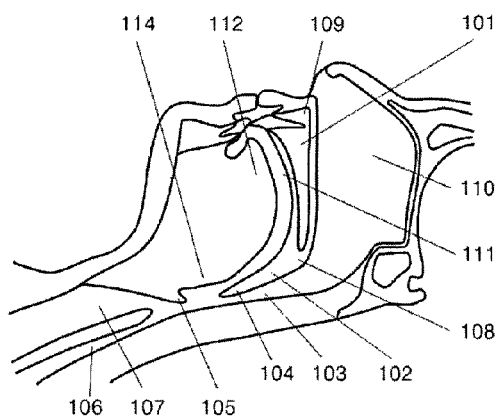
FIG. 1 is a cross-sectional side view of a human head during nasal breathing.

FIG. 1 is a cross-sectional side view of a human head during nasal breathing. When a human is breathing, a soft palate 102 naturally falls, an epiglottis 105 opens, and air may enter a trachea 107 via a nasal cavity 110 or an oral cavity 111 during mouth breathing.

Figure 2:
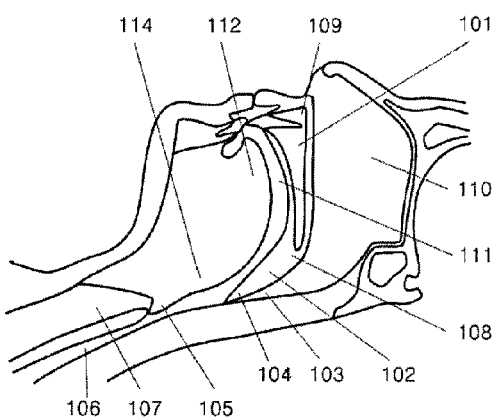
FIG. 2 is a cross-sectional side view of a human head during swallowing.

FIG. 2 is a cross-sectional side view of a human head during swallowing. When a human is swallowing, the soft palate 102 moves backwards, and a nasopharynx 103 is blocked. At the same time, the epiglottis 105 blocks the trachea 107, and food enters an esophagus 106 via a pharynx.

Figure 3:
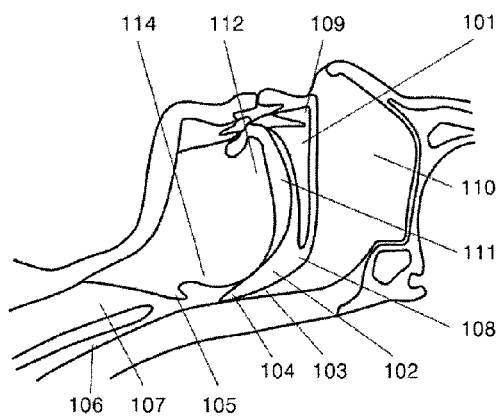
FIG. 3 is a view depicting occurrence of OSAHS in a patient.

FIG. 3 is a view depicting occurrence of OSAHS in a patient. When OSAHS occurs in a patient, soft tissues of the upper airway collapse, and the upper airway is obstructed, resulting in insufficient airflow and even apnea. Specifically, when OSAHS occurs, the soft palate 102 of the patient collapses backwards, so that a passage between the soft palate 102 and the nasopharynx 103 becomes narrow or is blocked, and at the same time soft tissues of a tongue root collapse, and thus, a passage between the tongue root 114 and the soft palate 102 becomes narrow or is blocked, resulting in insufficient airflow during breathing and even apnea. For some OSAHS patients, the collapse of the soft palate 102 not only directly causes that the passage between the soft palate 102 and the nasopharynx 103 is narrow or is blocked, but also directly causes that the passage between the tongue root 114 and the soft palate 102 is narrow or is blocked, resulting in insufficient airflow during breathing or apnea.

In view of the cause of disease that snoring and OSAHS are caused by the relaxation and collapse of the soft palate portion, the concept of the present invention is: to design an implant with one end fixed to a hard palate and the other end implanted into a soft palate, so as to lift a relaxed and collapsed soft palate and a part of soft tissues of a tongue root. A central axis of the soft palate during natural swinging is changed by lifting the soft palate towards the tongue root, so as to enlarge an airway of a pharynx during breathing, thereby achieving the objectives of treating snoring and OSAHS. Since swallowing occurs frequently in a non-sleep state, especially when eating, and swallowing occurs less frequently during sleep, an adjustable soft palate support is disclosed in the present invention.

The adjustable soft palate support of the present invention is a flat implant made of a material capable of being implanted into a human body for a long term, and includes a hard palate connecting end 1 and a support 2. The support 2 is a flat implant capable of being inserted into a soft palate. The hard palate connecting end includes a connecting structure 11 for fixing the support 115 of the present invention to a hard palate and an adjustment mechanism 12 for controlling the movement or a curvature of the support 2 or a lifting degree of the soft palate. The support 2 is connected to the hard palate connecting end 1, and the adjustment mechanism 12 on the hard palate connecting end 1 controls the movement or the curvature of the support 2 or the lifting degree of the soft palate.

Figure 4:
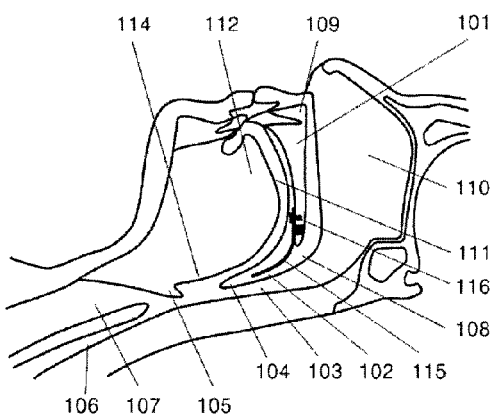
FIG. 4 is a view depicting the principle of a method for treating OSAHS according to the present invention and the working principle of an adjustable soft palate support of the present invention.

With the adjustable soft palate support of the present invention, since the hard palate connecting end 1 is fixed to a hard palate 101, and the support 2 is implanted into a muscular layer of the soft palate, the relaxed and collapsed soft palate 102 and a part of the soft tissues of the tongue root are lifted by using the hard palate 101 as a supporting point. The central axis of the soft palate during natural swinging is changed by lifting the soft palate towards the tongue root, so as to enlarge an airway of a pharynx during breathing, thereby achieving the objectives of treating snoring and OSAHS. Since swallowing occurs frequently in a non-sleep state, especially when eating, the adjustment mechanism 12 of the adjustable soft palate support may be adjusted to be in an "on" state, so that the support 2 implanted into the soft palate can move with natural swinging of the soft palate 102, so as to reduce interference with swallowing; and before sleep, the adjustment mechanism 12 of the adjustable soft palate support is adjusted to be in an off state, so that the support 2 implanted into the soft palate can lift the soft palate. The central axis of the soft palate during natural swinging is changed by lifting the soft palate towards the tongue root, so as to enlarge the airway of the pharynx during breathing. Thereby, the occurrence of snoring and OSAHS is avoided. See FIG. 4.

Further, an adjustable soft palate support allowing for multi-stage adjustment and continuous adjustment is designed in the present invention. In this way, the support 2 implanted into the soft palate may be adjusted to a suitable position by adjusting a control key 125 implanted on the hard palate with a finger, an apex of tongue or a remote controller. Therefore, normal swallowing can be ensured in the non-sleep state, and the soft palate can be effectively lifted in the sleep state to maintain a smooth upper airway during sleep, thereby avoiding the occurrence of snoring and OSAHS.

Figure 5:
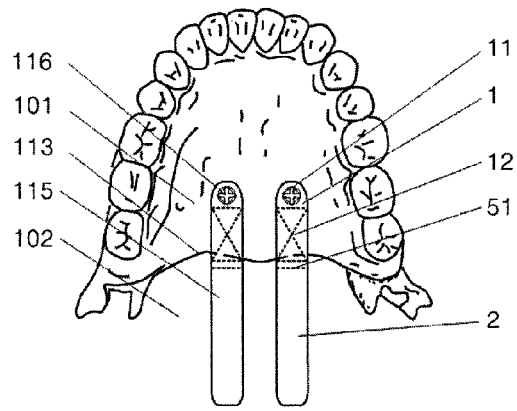
FIG. 5 is a schematic structural view of implanting an adjustable soft palate support of the present invention into a hard palate and a soft palate by fixing with one screw.
Figure 6:
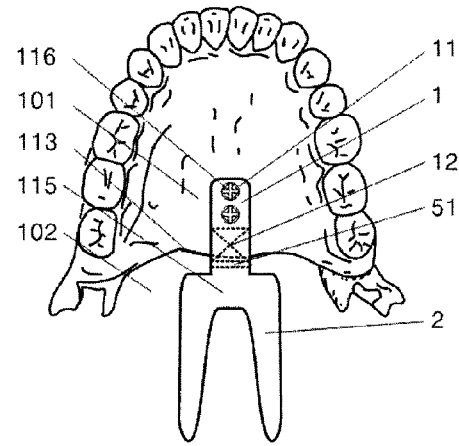
FIG. 6 is a schematic structural view of implanting an adjustable soft palate support of the present invention into a hard palate and a soft palate by fixing with two screws.
Figure 7:
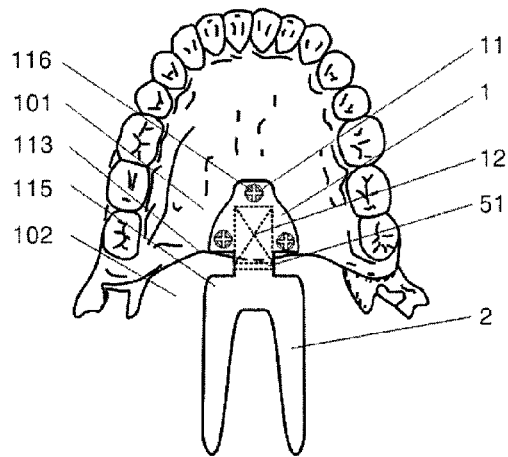
FIG. 7 is a schematic structural view of implanting an adjustable soft palate support of the present invention into a hard palate and a soft palate by fixing with three screws.

The adjustable soft palate support of the present invention is skillfully designed, and a surgery may be performed under local anesthesia or general anesthesia. During the surgery, the adjustable soft palate supports of the present invention of different sizes are selected according to the severity of snoring and OSAHS. The surgery can be completed simply by making a small incision of 2 mm to 20 mm at the hard palate of the oral cavity, fixing the hard palate connecting end 1 of the adjustable soft palate support of the present invention to the hard palate 101, inserting the support 2 into the muscular layer of the soft palate 102, and suturing the incision. Thus, the objective of minimally invasive treatment of snoring and OSAHS is realized. Clinically, the adjustable soft palate support of the present invention may be implanted into the hard palate and the soft palate by fixing with one screw, see FIG. 5; or the adjustable soft palate support of the present invention may be implanted into the hard palate and the soft palate by fixing with two screws, see FIG. 6; or the adjustable soft palate support of the present invention may be implanted into the hard palate and the soft palate by fixing with three screws, see FIG. 7. The method and implanted instrument of the present invention have the advantages of small wound, fast recovery, immediate effect, and reliable efficacy. Especially, the patient may conveniently adjust the degree of lifting the soft palate by the soft palate support according to his or her feeling after surgery, so as to achieve optimal treatment effect and comfort.

Embodiment 1

A Pushrod-Type Adjustable Soft Palate Support of the Present Invention

Based on the technical solution of the present invention, the product of the present invention is manufactured by selecting medical grade titanium and a medical titanium alloy capable of being implanted into a human body for a long term according to a common process procedure of titanium metal products.

Figure 8:
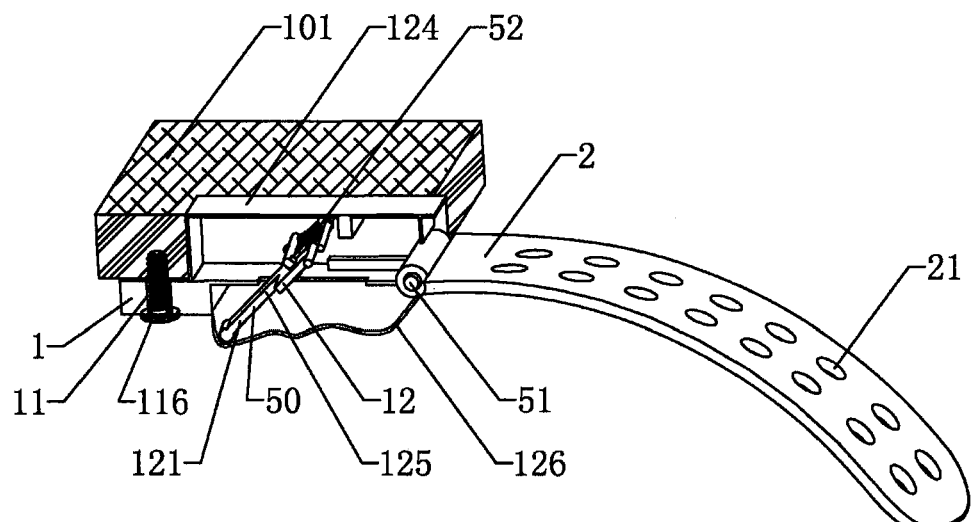
FIG. 8 is a schematic structural view of a pushrod-type adjustable soft palate support of the present invention being in an "on" state, in which in this embodiment, the adjustment mechanism 12 adopts a spring pushrod-type switch structure, and when a pushrod 50 is pushed towards incisors, the adjustment mechanism 12 on the hard palate connecting end 1 is in an "on" state, and the support 2 can freely rotate around a rotating shaft 51, so that the support 2 can swing with the swinging of the soft palate in an unconstrained manner.
Figure 9:
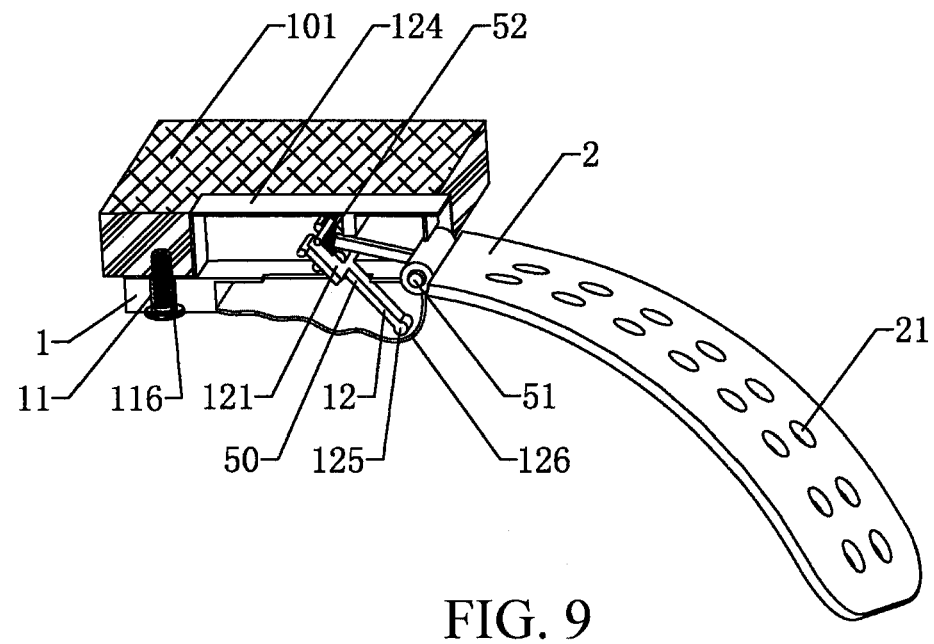
FIG. 9 is a schematic structural view of a pushrod-type adjustable soft palate support of the present invention being in an "off" state, in which in this embodiment, the adjustment mechanism 12 adopts a spring pushrod-type switch structure, and when a pushrod 50 is pushed towards a tongue root, the adjustment mechanism 12 on the hard palate connecting end 1 is in an "off" state, the support 2 is constrained and cannot freely rotate around a rotating shaft 51, so that the support 2 lifts a soft palate towards the tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Referring to FIG. 8 to FIG. 9, a basic structure of the pushrod-type adjustable soft palate support of the present invention is as follows.

Support 2:

a titanium metal plate with a thickness of 0.6 mm to 1 mm is adopted, the titanium metal plate is bent to have a radian matching a natural curvature when the soft palate of the human body relaxes, and a tiny through hole 21 is formed on the titanium metal plate, in which the tiny through hole 21 has a diameter of 0.5 mm to 2 mm, which facilitates tissue growth and penetration.

Hard palate connecting end 1: the hard palate connecting end 1 is made of titanium metal.

Connecting structure 11: in this embodiment, a through hole allowing a screw with a diameter of 4 mm to pass through is formed on the hard palate connecting end 1, and is used as a connecting structure 11. The adjustable soft palate support 115 of the present invention may be fixed to the hard palate 101 through the connecting structure 11 by using a titanium fastening screw 116.

Adjustment mechanism 12: in this embodiment, the adjustment mechanism 12 adopts a spring pushrod-type switch structure. The adjustment mechanism 12 includes a pushrod 50, a rotating shaft 51, a position restoring spring 52, an adjustment rod 60, a positioning block 58, a housing 124, and a medical-purpose flexible material film 126. The pushrod 50 not only forms a switch structure 121 with the position restoring spring 52 and the adjustment rod 60, but is also used as an adjustment control key 125.

In a non-sleep state, when the pushrod 50 is pushed towards incisors, the adjustment mechanism 12 on the hard palate connecting end 1 is in an "on" state, and the support 2 can freely rotate around the rotating shaft 51, so that the support 2 can swing with the swinging of the soft palate in an unconstrained manner. See FIG. 8.

Before sleep, when the pushrod 50 is pushed towards the tongue root with a finger or an apex of tongue, the adjustment mechanism 12 on the hard palate connecting end 1 is in an "off" state, and the support 2 is constrained and cannot freely rotate around the rotating shaft 51, so that the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 9.

In addition, the materials for manufacturing the support 2 include, but are not limited to, titanium metal, a titanium alloy, a Nitinol alloy, medical stainless steel, and other medical metal materials and medical polymer materials capable of being implanted into the human body for a long term.

The materials for manufacturing the hard palate connecting end 1 include, but are not limited to, titanium metal, a titanium alloy, a Nitinol alloy, medical stainless steel, and other medical metal materials and medical polymer materials capable of being implanted into the human body for a long term.

The flexible polymer materials for manufacturing the medical-purpose flexible material film 126 include, but are not limited to, medical silica gel, medical polyurethane, and other elastic polymer materials capable of being implanted into the human body for a long term.

The materials for manufacturing the fastener 116 include, but are not limited to, titanium metal, a titanium alloy, a Nitinol alloy, medical stainless steel, and other medical metal materials and medical polymer materials capable of being implanted into the human body for a long term.

Embodiment 2

A Double Button Type Adjustable Soft Palate Support of the Present Invention

Based on the technical solution of the present invention, the product of the present invention is manufactured by selecting a medical metal material capable of being implanted into a human body for a long term according to a common process procedure of medical metal products.

Figure 10:
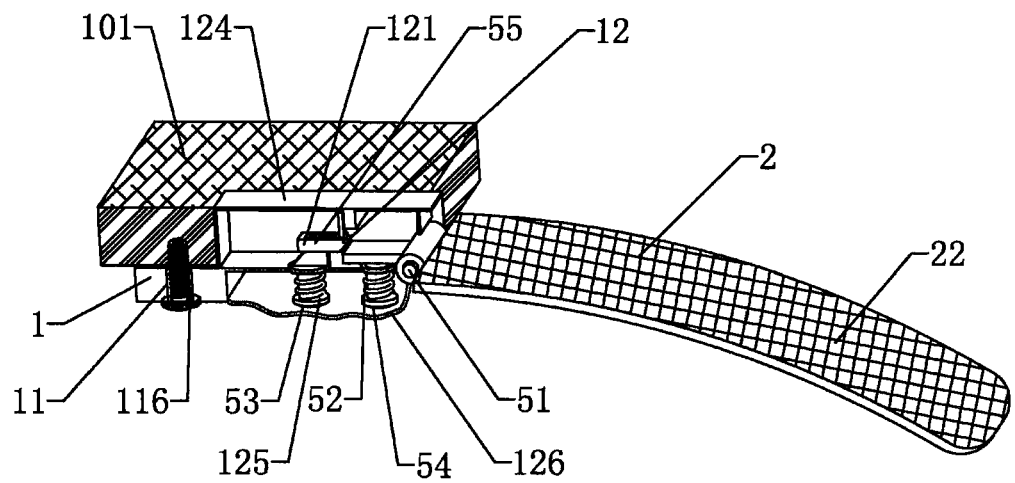
FIG. 10 is a schematic structural view of a double button type adjustable soft palate support of the present invention being in an "on" state, in which in this embodiment, the adjustment mechanism 12 adopts a double button type switch structure, and when a button 53 close to incisors is pressed, the adjustment mechanism 12 on the hard palate connecting end 1 is in an "on" state, and the support 2 can freely rotate around a rotating shaft 51, so that the support 2 can swing with the swinging of the soft palate in an unconstrained manner.
Figure 11:
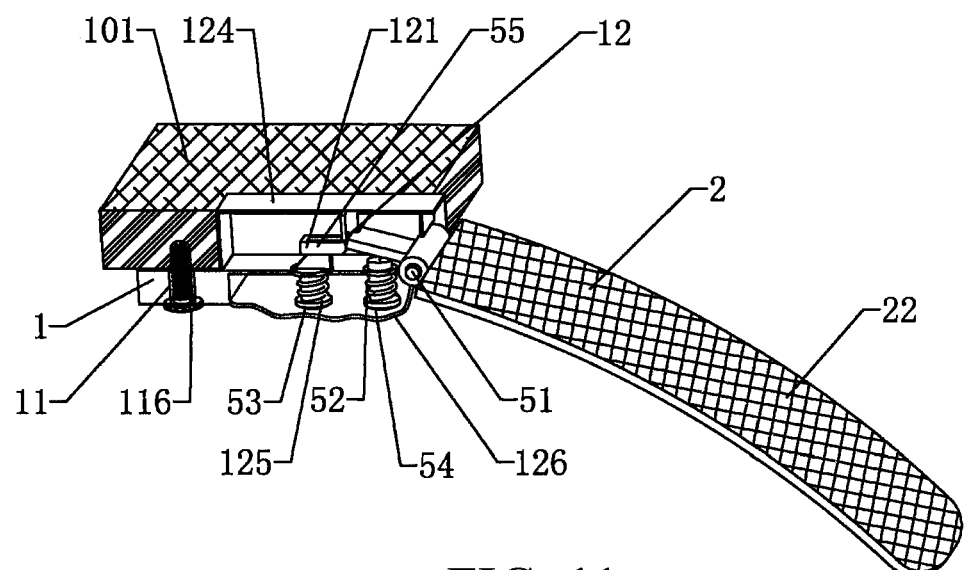
FIG. 11 is a schematic structural view of a double button type adjustable soft palate support of the present invention being in an "off" state, in which in this embodiment, the adjustment mechanism 12 adopts a double button type switch structure, and when a button 54 close to a tongue root is pressed, the adjustment mechanism 12 on the hard palate connecting end 1 is in an "off" state, the support 2 is constrained and cannot freely rotate around a rotating shaft 51, so that the support 2 lifts a soft palate towards the tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Referring to FIG. 10 to FIG. 11, a basic structure of the double button type adjustable soft palate support of the present invention is as follows.

Support 2: a titanium-nickel shape memory alloy plate with a thickness of 0.6 mm to 1 mm is adopted, and the titanium-nickel shape memory alloy plate is thermally set to have a radian matching a natural curvature when the soft palate of the human body relaxes, and convex-concave texture or a rough surface 22 is formed on the surface thereof, so as to facilitate tissue growth and attachment.

Hard palate connecting end 1: the hard palate connecting end 1 is made of titanium metal.

Connecting structure 11: in this embodiment, a through hole allowing a screw with a diameter of 4 mm to pass through is formed on the hard palate connecting end 1, and is used as a connecting structure 11. The adjustable soft palate support 115 of the present invention may be fixed to the hard palate 101 through the connecting structure 11 by using a titanium fastening screw 116.

Adjustment mechanism 12: in this embodiment, the adjustment mechanism 12 adopts a double button type switch structure. The adjustment mechanism 12 includes a button 53 close to incisors, a button 54 close to a tongue root, a multi-stage positioning block 55, a rotating shaft 51, a position restoring spring 52, an adjustment rod 60, a positioning block 58, a housing 124, and a medical-purpose flexible material film 126. The button 53 close to incisors and the button 54 close to the tongue root not only form a switch structure 121 with the position restoring spring 52, the adjustment rod 60, and the multi-stage positioning block 55, but are also used as an adjustment control key 125.

In a non-sleep state, when the button 53 close to incisors is pressed, the adjustment mechanism 12 on the hard palate connecting end 1 is in an "on" state, and the support 2 can freely rotate around the rotating shaft 51, so that the support 2 can swing with the swinging of the soft palate in an unconstrained manner. See FIG. 10.

Before sleep, when the button 54 close to the tongue root is pressed, the adjustment mechanism 12 on the hard palate connecting end 1 is in an "off" state, and the support 2 is constrained and cannot freely rotate around the rotating shaft 51, so that the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 11.

Embodiment 3

A Rotary Multi-Stage Type Adjustable Soft Palate Support of the Present Invention Based on the technical solution of the present invention, the product of the present invention is manufactured by selecting a medical metal material capable of being implanted into a human body for a long term according to a common process procedure of medical metal products.

Figure 12:
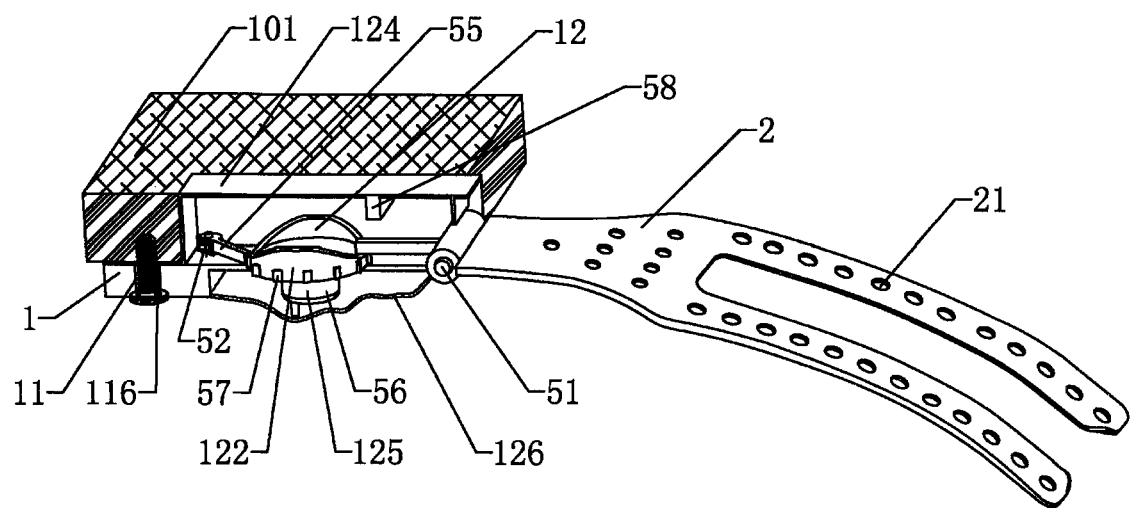
FIG. 12 is a schematic structural view of a rotary multi-stage type adjustable soft palate support of the present invention being in an "on" state, in which in this embodiment, the adjustment mechanism 12 adopts a rotary switch type multi-stage structure; and a rotary switch is rotated to enable the support 2 to move in a large range, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner.
Figure 13:
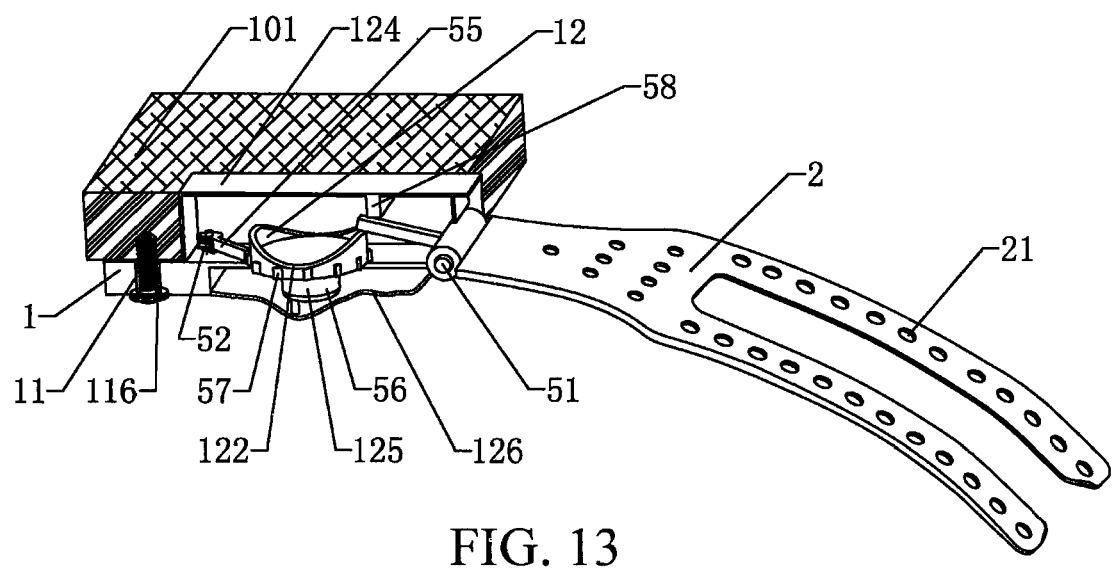
FIG. 13 is a schematic structural view of a rotary multi-stage type adjustable soft palate support of the present invention being in an "off" state, in which in this embodiment, the adjustment mechanism 12 adopts a rotary multi-stage type positioning structure; a rotary switch is rotated to limit the support 2 to move in a small range, that is, the adjustment mechanism 12 on the hard palate connecting end 1 is in an "off" state, and degrees of lifting a soft palate by the support 2 are different corresponding to different positions; since the support 2 is constrained and cannot freely rotate around a rotating shaft 51 in a large range, the support 2 lifts the soft palate towards a tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Referring to FIG. 12 to FIG. 13, a basic structure of the rotary multi-stage type adjustable soft palate support of the present invention is as follows.

Support 2: a titanium-nickel shape memory alloy plate with a thickness of 0.6 mm to 1 mm is adopted, and a tiny through hole 21 is formed on the metal plate, in which the tiny through hole 21 has a diameter of 0.5 mm to 2 mm, which facilitates tissue growth and penetration. The titanium-nickel shape memory alloy plate is thermally set to have a radian matching a natural curvature when the soft palate of the human body relaxes.

Hard palate connecting end 1: the hard palate connecting end 1 is made of titanium metal.

Connecting structure 11: in this embodiment, a through hole allowing a screw with a diameter of 4 mm to pass through is formed on the hard palate connecting end 1, and is used as a connecting structure 11. The adjustable soft palate support 115 of the present invention may be fixed to the hard palate 101 through the connecting structure 11 by using a titanium fastening screw 116.

Adjustment mechanism 12: in this embodiment, the adjustment mechanism 12 adopts a rotary switch type multi-stage structure. The adjustment mechanism 12 includes a rotary adjustment switch 56, a multi-stage positioning block 55, a rotating shaft 51, a position restoring spring 52, an adjustment rod 60, a positioning block 58, a housing 124, and a medical-purpose flexible material film 126. The rotary adjustment switch 56 not only forms a switch structure 121 with the multi-stage positioning block 55, the position restoring spring 52, and the adjustment rod 60, but is also used as an adjustment control key 125.

In a non-sleep state, the rotary adjustment switch 56 is rotated to enable the support 2 to move in a large range, that is, the adjustment mechanism 12 on the hard palate connecting end 1 is in an "on" state, and the support 2 can freely rotate around the rotating shaft 51, so that the support 2 can swing with the swinging of the soft palate in an unconstrained manner. See FIG. 12.

Before sleep, the rotary adjustment switch 56 is rotated to limit the support 2 to move in a small range, that is, the adjustment mechanism 12 on a hard palate connecting end 1 is in an "off" state, and degrees of lifting the soft palate by the support 2 are different corresponding to different positions. Since the support 2 is constrained and cannot freely rotate around the rotating shaft 51 in a large range, the support 2 lifts the soft palate towards a tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 13.

Embodiment 4

A Double-Button Three-Position Adjustable Soft Palate Support of the Present Invention In this embodiment, the adjustment mechanism 12 adopts a double-button three-position structure, which has basically the same structure as that of Embodiment 2, and the differences lie in that:

First, an elastic module 20 and a rigid module 40 are alternately mounted on a tail portion of the support 2, so as to improve the flexibility of the tail portion of the support 2.

Second, the adjustment mechanism 12 adopts a double button type three-position structure, a multi-stage adjustment positioning slot 57 and a multi-stage positioning block 55 are manufactured on a member, and three positions may be used for adjustment. Movement ranges of the support 2 and lifting degrees of the soft palate are different corresponding to different positions.

Figure 14:
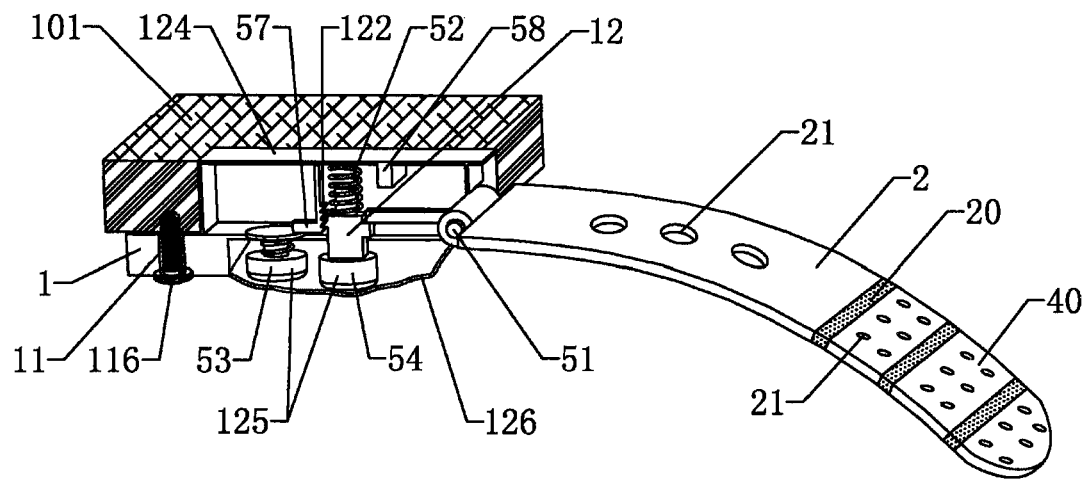
FIG. 14 is a schematic structural view of a double-button three-position adjustable soft palate support of the present invention being in an "on" state, in which in this embodiment, the adjustment mechanism 12 adopts a double button type three-position structure, and when a button 53 close to incisors is pressed, the adjustment mechanism 12 on the hard palate connecting end 1 is in an "on" state, and the support 2 can freely rotate around a rotating shaft 51, so that the support 2 can swing with the swinging of the soft palate in an unconstrained manner.
Figure 15:
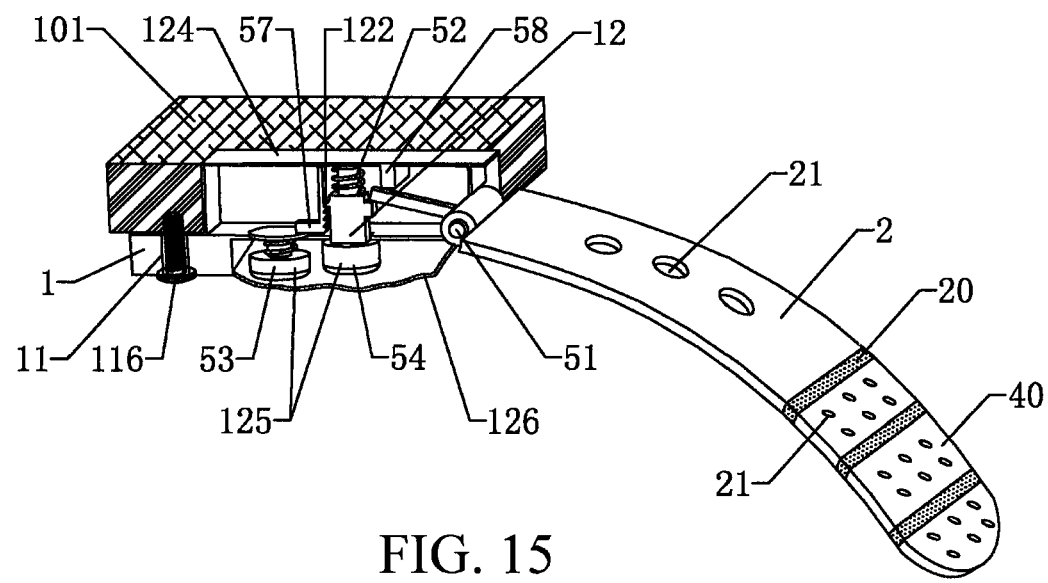
FIG. 15 is a schematic structural view of a double-button three-position adjustable soft palate support of the present invention being in an "off" state, in which in this embodiment, the adjustment mechanism 12 adopts a double-button three-position switch structure, and when a button 54 close to a tongue root is pressed, the adjustment mechanism 12 on the hard palate connecting end 1 is in an "off" state of different positions in sequence, and degrees of lifting a soft palate by the support 2 are different corresponding to different positions; since the support 2 is constrained and cannot freely rotate around a rotating shaft 51, the support 2 lifts the soft palate towards the tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

In a non-sleep state, when the button 53 close to incisors is pressed, the adjustment mechanism 12 on the hard palate connecting end 1 is in an "on" state, and the support 2 can freely rotate around the rotating shaft 51, so that the support 2 can swing with the swinging of the soft palate in an unconstrained manner. See FIG. 14.

Before sleep, when the button 54 close to the tongue root is pressed, the adjustment mechanism 12 on the hard palate connecting end 1 is in an "off" state of different positions in sequence, and degrees of lifting the soft palate by the support 2 are different corresponding to different positions. Since the support 2 is constrained and cannot freely rotate around the rotating shaft 51, the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Embodiment 5

A Rectilinear Translation Type Continuously Adjustable Soft Palate Support of the Present Invention The feature of the present invention lies in that, the adjustment mechanism 12 adopts a slide block type continuous adjustment mechanism, and the degree of lifting the soft palate by the support 2 is continuously adjusted through parallel translation of a slide block 59.

In addition, an elastic module 20 of a tail portion of the support 2 adopts a close-packed coil spring structure.

Figure 16:
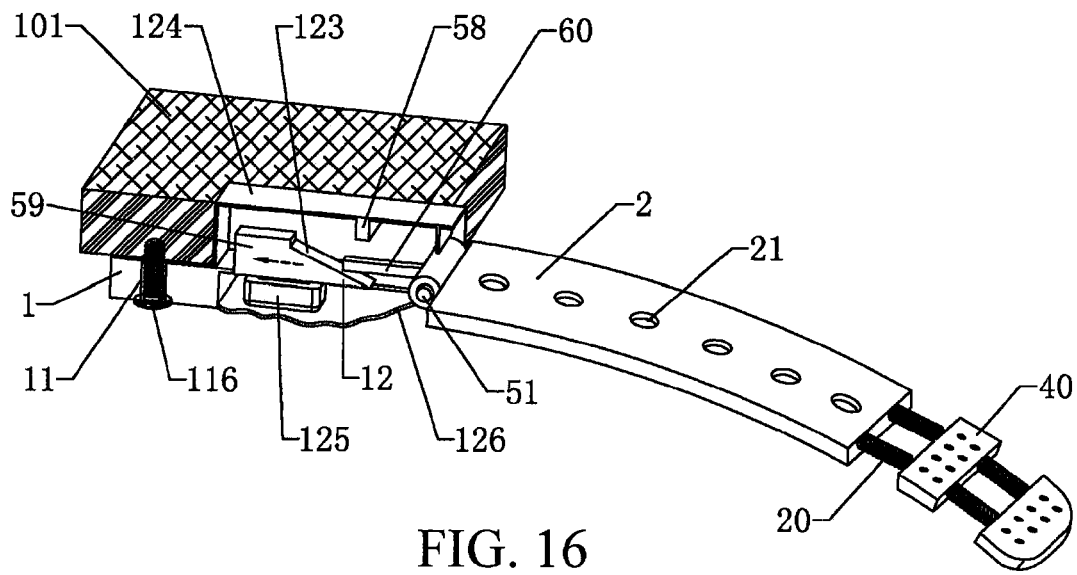
FIG. 16 is a schematic structural view of a rectilinear translation type continuously adjustable soft palate support of the present invention being in an "on" state, in which in this embodiment, the adjustment mechanism 12 adopts a slide block type continuous positioning mechanism, and a slide block 59 is pushed rectilinearly towards incisors to enable the support 2 to move in a large range, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner.

In a non-sleep state, the slide block 59 is pushed rectilinearly towards incisors to enable the support 2 to move in a large range, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner. See FIG. 16.

Figure 17:
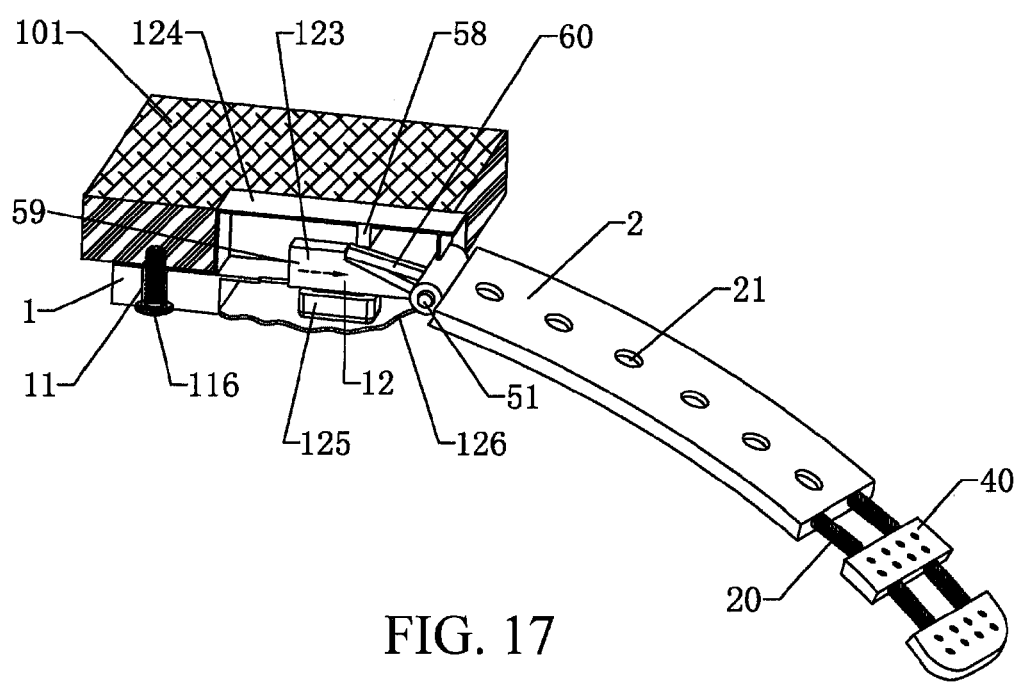
FIG. 17 is a schematic structural view of a rectilinear translation type continuously adjustable soft palate support of the present invention being in an "off" state, in which in this embodiment, the adjustment mechanism 12 adopts a slide block type continuous positioning mechanism, and a slide block 59 is pushed rectilinearly towards a tongue root to limit the support 2 to move in a small range, that is, the adjustment mechanism 12 on the hard palate connecting end 1 is in an "off" state, and degrees of lifting a soft palate by the support 2 are different corresponding to different positions; since the support 2 is constrained and cannot freely rotate around a rotating shaft 51 in a large range, the support 2 lifts the soft palate towards a tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

In a sleep state, the slide block 59 is pushed rectilinearly towards the tongue root to limit the support 2 to move in a small range, that is, the adjustment mechanism 12 on the hard palate connecting end 1 is in an "off" state, and degrees of lifting the soft palate by the support 2 are different corresponding to different positions. Since the support 2 is constrained and cannot freely rotate around the rotating shaft 51 in a large range, the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 17.

Embodiment 6

A Screw-Thread Type Continuously Adjustable Soft Palate Support of the Present Invention The difference of this embodiment lies in that, the adjustment mechanism 12 adopts a screw-thread positioning mechanism, and by rotating an adjustment screw rod 61, the movement or the curvature of the support 2 or the lifting degree of the soft palate may be conveniently controlled.

In addition, an elastic module 20 of a tail portion of the support 2 adopts a close-packed coil spring structure coated with a medical flexible polymer material.

Figure 18:
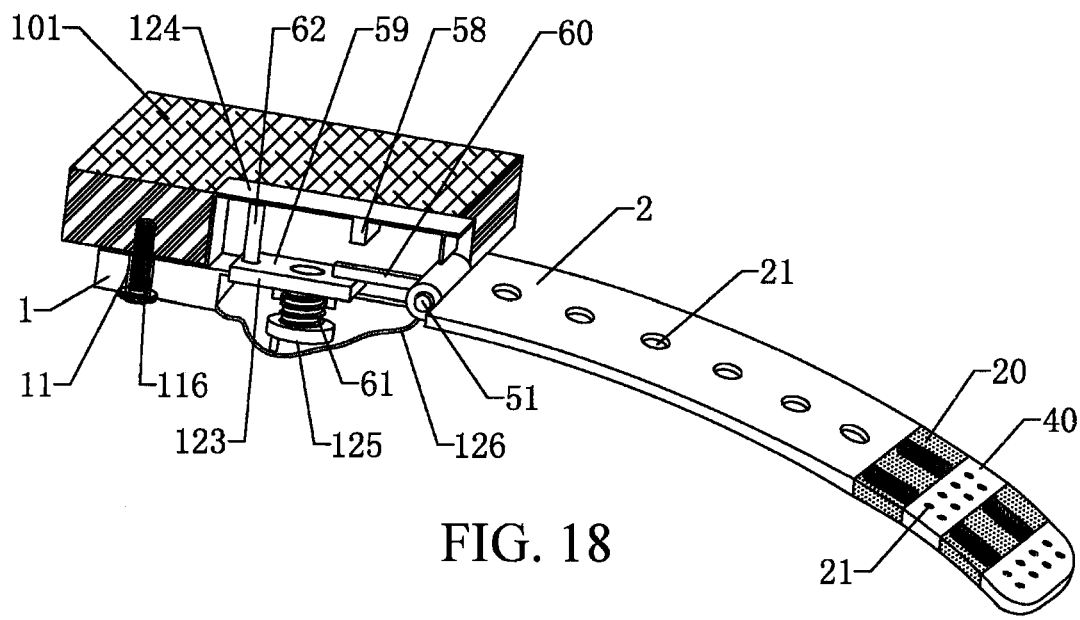
FIG. 18 is a schematic structural view of a screw-thread type continuously adjustable soft palate support of the present invention being in an "on" state, in which in this embodiment, the adjustment mechanism 12 adopts a screw-thread positioning mechanism; and an adjustment screw rod 61 is rotated outwards to enable the support 2 to move in a large range, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner.

The adjustment mechanism 12 of this embodiment includes an adjustment screw rod 61, a guide rod 62, a positioning slide block 59, a positioning block 58, a rotating shaft 51, an adjustment rod 60, a housing 124, and a medical-purpose flexible material film 126. The adjustment screw rod 61 not only forms a continuous adjustment mechanism 123 with the guide rod 62, the positioning slide block 59, the positioning block 58, and the adjustment rod 60, but is also used as an adjustment control key 125. See FIG. 18.

In a non-sleep state, the adjustment screw rod 61 is rotated outwards to enable the support 2 to move in a large range, that is, the adjustment mechanism 12 on the hard palate connecting end 1 is in an "on" state, and the support 2 can freely rotate around the rotating shaft 51, so that the support 2 can swing with the swinging of the soft palate in an unconstrained manner. See FIG. 18.

Figure 19:
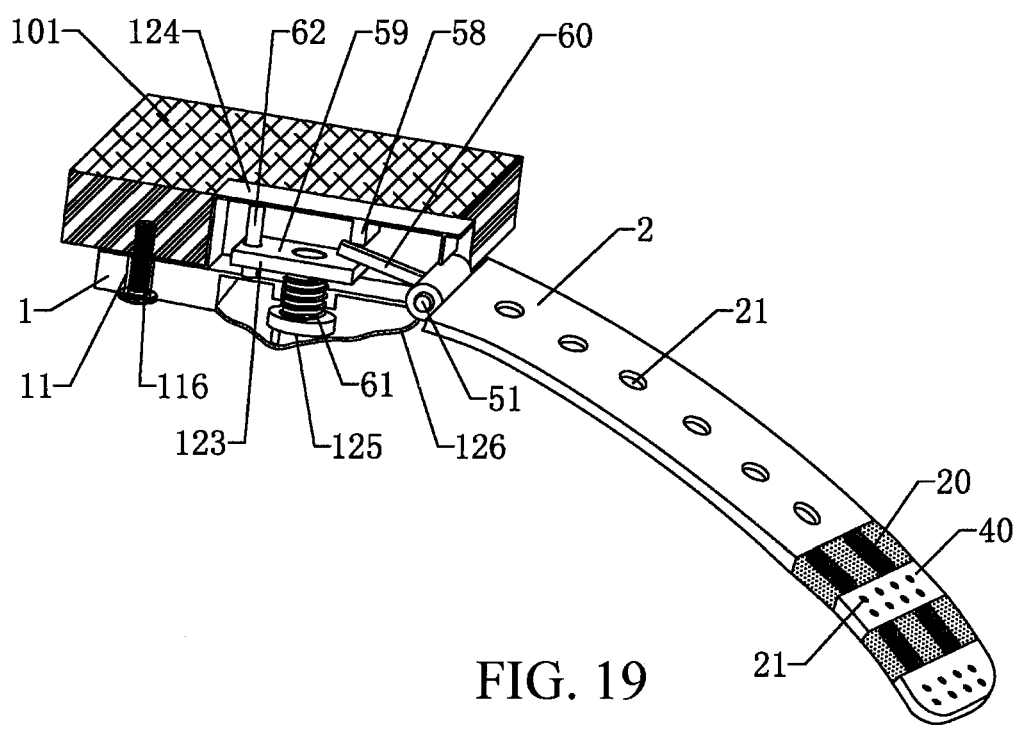
FIG. 19 is a schematic structural view of a screw-thread type continuously adjustable soft palate support of the present invention being in an "off" state, in which in this embodiment, the adjustment mechanism 12 adopts a screw-thread positioning mechanism; an adjustment screw rod 61 is rotated inwards to limit the support 2 to move in a small range, that is, the adjustment mechanism 12 on the hard palate connecting end 1 is in an "off" state, and degrees of lifting a soft palate by the support 2 are different corresponding to different positions; since the support 2 is constrained and cannot freely rotate around a rotating shaft 51 in a large range, the support 2 lifts the soft palate towards a tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Before sleep, the adjustment screw rod 61 is rotated inwards to limit the support 2 to move in a small range, that is, the adjustment mechanism 12 on the hard palate connecting end 1 is in an "off" state, and degrees of lifting the soft palate by the support 2 are different corresponding to different positions. Since the support 2 is constrained and cannot freely rotate around the rotating shaft 51 in a large range, the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 19.

Embodiment 7

An Electrically Adjustable Soft Palate Support of the Present Invention

In this embodiment, the adjustment mechanism 12 adopts an electrical positioning mechanism. The adjustment mechanism 12 includes a power supply 65, a circuit 68, an electrical device 63, a transmission mechanism 66, and an electrical adjustment control switch 64, and the power supply 65, the circuit 68, the electrical device 63, and the transmission mechanism 66 are built inside a housing 124 of the adjustment mechanism. The electrical adjustment control switch 64 is on the housing 124, and is coated with a medical-purpose flexible material film 126.

Figure 20:
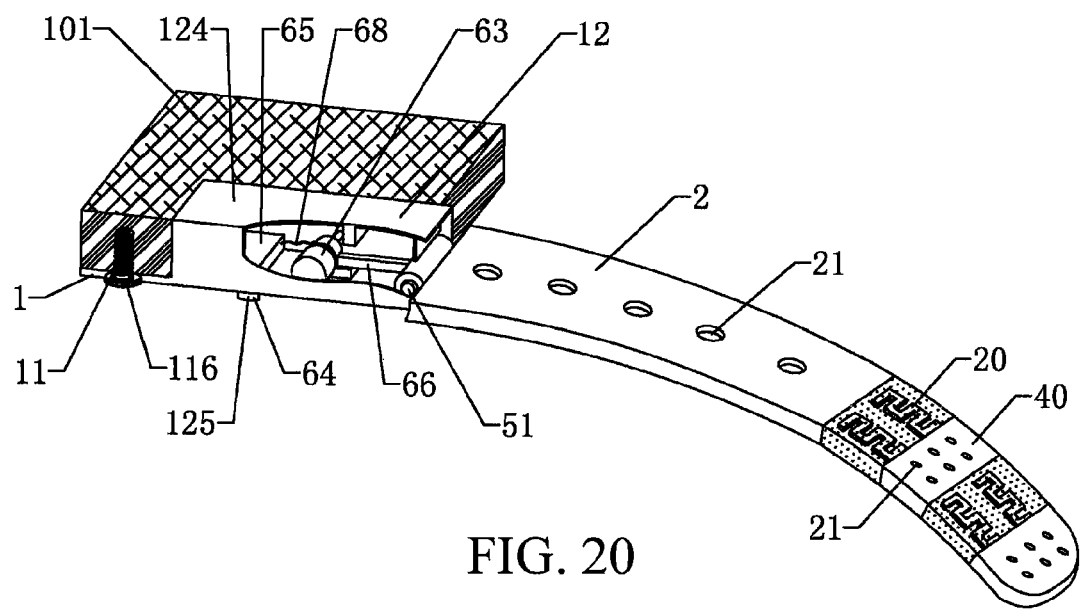
FIG. 20 is a schematic structural view of an electrically adjustable soft palate support of the present invention being in an "on" state, in which in this embodiment, the adjustment mechanism 12 adopts an electrical positioning mechanism; and an electrical adjustment control switch 64 is pressed, and an electrical device 63, driven by a built-in power supply 65, enables the support 2 to move in a large range through a transmission mechanism 66, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner.

In a non-sleep state, the electrical adjustment control switch 64 is pressed, and the electrical device 63, driven by the built-in power supply 65 and circuit 68, enables the support 2 to move in a large range through the transmission mechanism 66, that is, the adjustment mechanism 12 on the hard palate connecting end 1 is in an "on" state, and the support 2 can freely rotate around a rotating shaft 51, so that the support 2 can swing with the swinging of the soft palate in an unconstrained manner. See FIG. 20.

Figure 21:
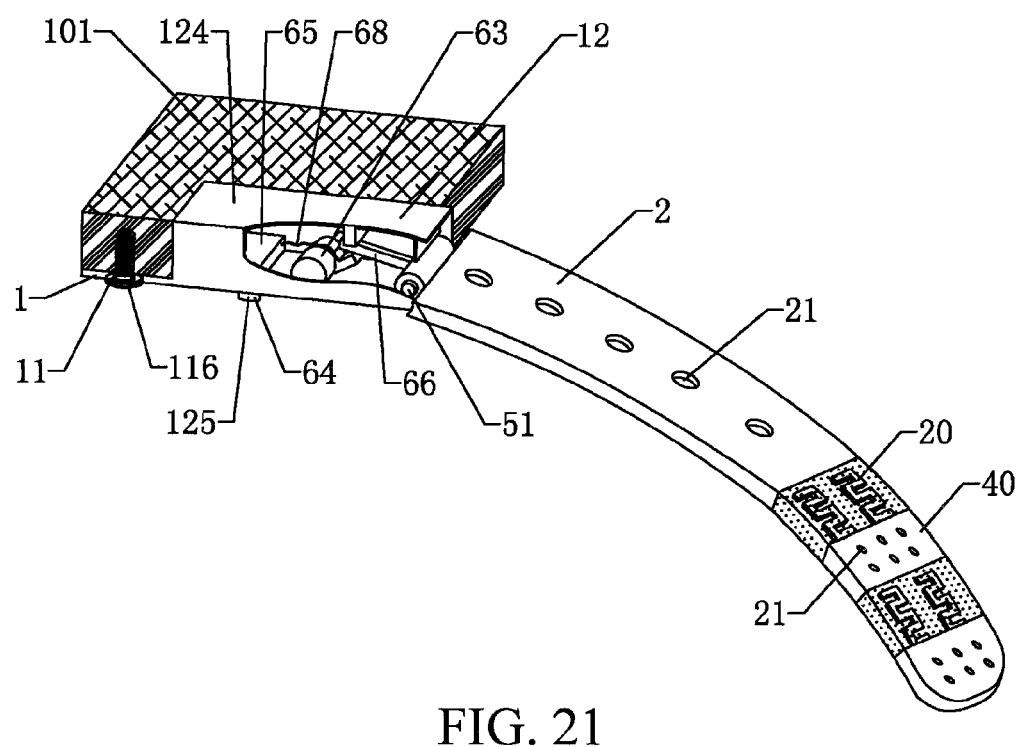
FIG. 21 is a schematic structural view of a screw-thread type continuously adjustable soft palate support of the present invention being in an "off" state, in which in this embodiment, the adjustment mechanism 12 adopts an electrical positioning mechanism; an electrical adjustment control switch 64 is pressed, and an electrical device 63, driven by a built-in power supply 65, enables the support 2 to move in a small range through a transmission mechanism 66, that is, the adjustment mechanism 12 on the hard palate connecting end 1 is in an "off" state, and the support 2 lifts a soft palate; since the support 2 is constrained and cannot freely rotate around a rotating shaft 51 in a large range, the support 2 lifts the soft palate towards a tongue root and changes a central axis of the soft palate during swinging; and soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS.

Before sleep, the electrical adjustment control switch 64 is pressed, and the electrical device 63, controlled and driven by the built-in power supply 65 and circuit 68, enables the support 2 to move in a small range through the transmission mechanism 66, that is, the adjustment mechanism 12 on the hard palate connecting end 1 is in an "off" state, and the support 2 lifts the soft palate. Since the support 2 is constrained and cannot freely rotate around the rotating shaft 51 in a large range, the support 2 lifts the soft palate towards the tongue root and changes a central axis of the soft palate during swinging. Soft tissues of the soft palate can still swing within a certain range, but the swinging is constrained to two sides of a supporting plane of the support 2, so that an airway at a pharynx is enlarged by lifting the soft palate and a part of the tongue root, thereby achieving the objectives of treating snoring and OSAHS. See FIG. 21.

Figure 22:
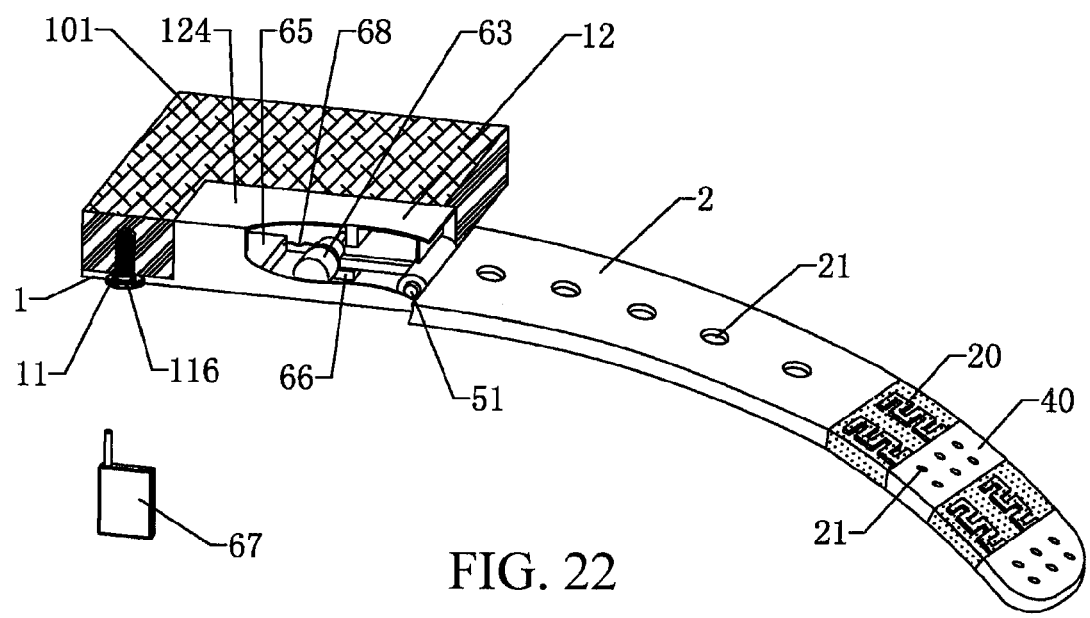
FIG. 22 is a schematic structural view of an electrically adjustable soft palate support of the present invention being in an "on" state, in which this embodiment is substantially the same as Embodiment 20, and the difference lies in replacing the built-in electrical adjustment control switch 64 with a remote controller 67.
Figure 23:
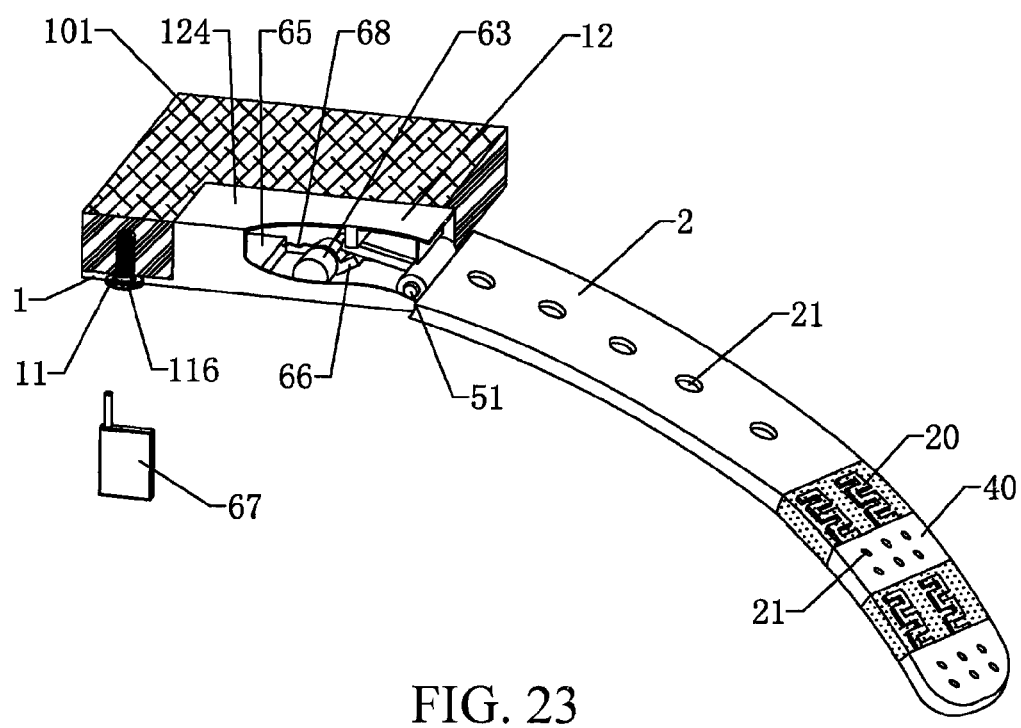
FIG. 23 is a schematic structural view of a screw-thread type continuously adjustable soft palate support of the present invention being in an "off" state, in which this embodiment is substantially the same as Embodiment 20, and the difference lies in replacing the built-in electrical adjustment control switch 64 with a remote controller 67.
Figure 24:
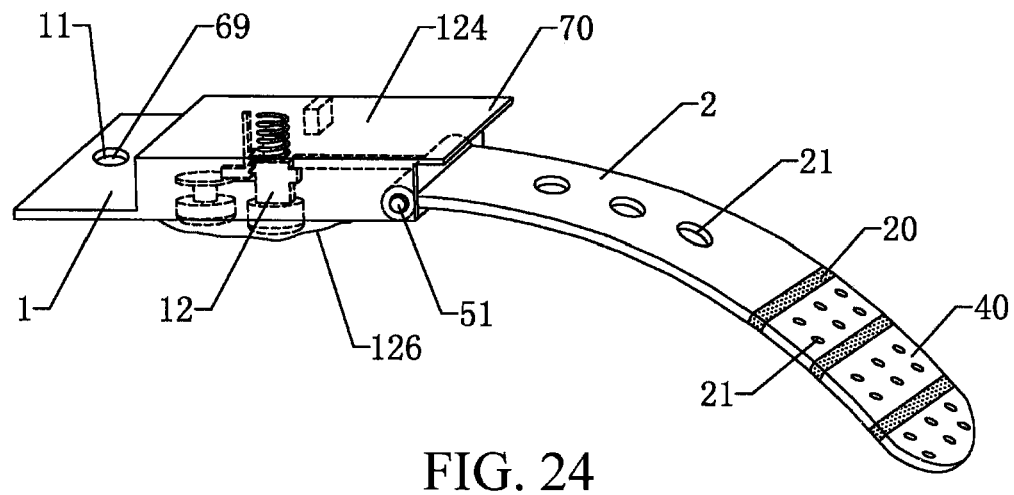
FIG. 24 is a schematic structural view of an adjustable soft palate support of the present invention, in which in this embodiment, the connecting structure 11 is a combination of a fastener through hole 69 and a locking edge 70; during assembly, a slot matching the hard palate connecting end 1 is opened on the hard palate 101, so as to accommodate the housing 124 of the adjustment mechanism 12; and the locking edge 70 is locked to one side of the hard palate 101 close to the nasal cavity, and a fastening screw 116 may be used to fix the hard palate connecting end 1 to the hard palate 101 through the fastener through hole 69.
Figure 25:
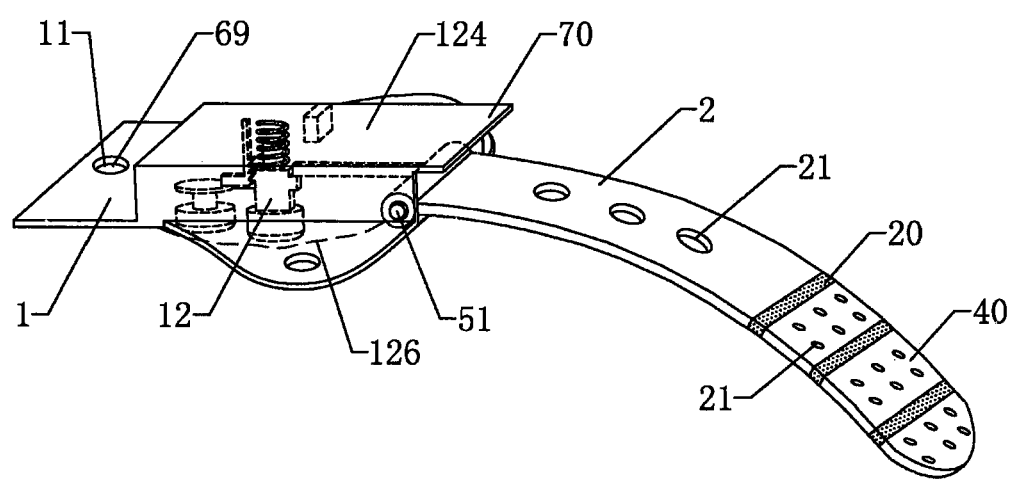
FIG. 25 is a schematic structural view of an adjustable soft palate support of the present invention, in which in this embodiment, the connecting structure 11 adopts a through hole structure, and three fastener through holes 69 for fixing the hard palate connecting end 1 to a hard palate are arranged at the bottom of the hard palate connecting end 1 in the form of a triangle, so as to form the connecting structure 11; and the hard palate connecting end 1 may be fixed to the hard palate 101 through the fastener through holes 69 by using fastening screws 116.
Figure 26:
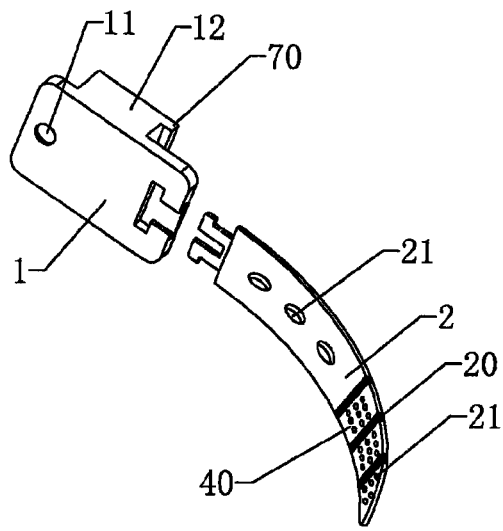
FIG. 26 is a schematic structural view of a combined-type adjustable soft palate support combined through convex-concave engagement of the present invention before being assembled.
Figure 27:
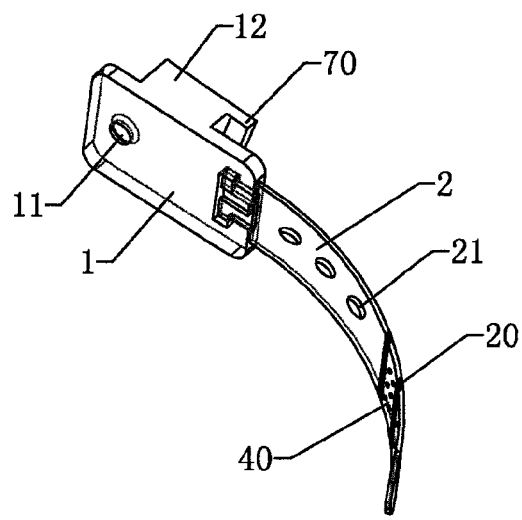
FIG. 27 is a schematic structural view of a combined-type adjustable soft palate support combined through convex-concave engagement of the present invention after being assembled.

In addition, this embodiment may be improved to be controlled by a remote controller. If the circuit 68 and the electrical adjustment control switch 64 are modified according to a wireless remote control mode, this embodiment may be controlled by a remote controller 67. See FIG. 22 to FIG. 23.

Embodiment 8

A Combined-Type Adjustable Soft Palate Support of the Present Invention

The difference of this embodiment lies in that, the hard palate connecting end 1 and the support 2 may be clinically implanted in stages.

Firstly, the hard palate connecting end 1 is fixed to the hard palate 101 via a fastener 116. Three months to six months later, the hard palate connecting end 1 will have been firmly fixed with the hard palate 101, and another surgery is performed, in which the support 2 is inserted into the soft palate 102, and at the same time, the near end of the support 2 and the adjustment mechanism 12 of the hard palate connecting end 1 are connected together through convex-concave engagement or a fastener. The advantage lies in that the hard palate connecting end 1 and the hard palate 102 are firmly connected, and the disadvantage lies in that it is necessary to perform two surgeries, which increases the medical expense of the patient. See FIG. 26 to FIG. 29, and FIG. 5 to FIG. 7.

Figure 28:
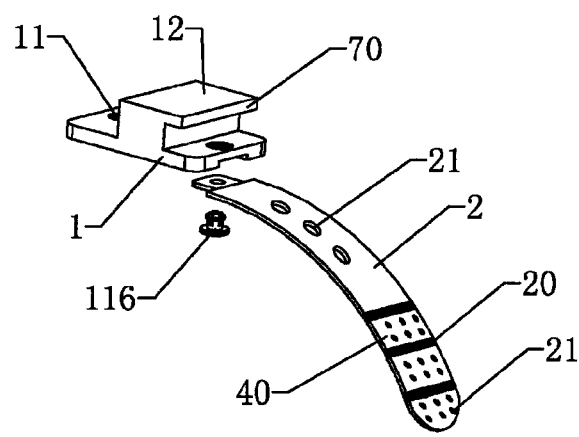
FIG. 28 is a schematic structural view of a screw-thread combined-type adjustable soft palate support of the present invention before being assembled.
Figure 29:
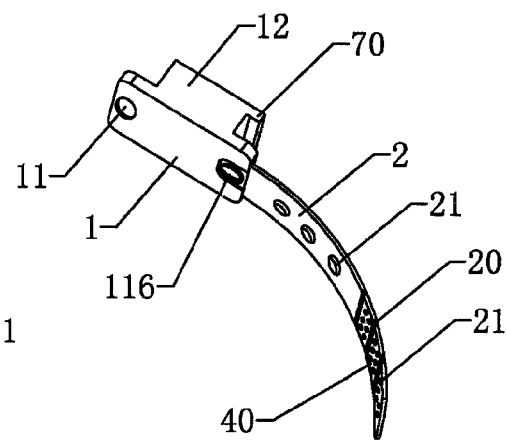
FIG. 29 is a schematic structural view of a screw-thread combined-type adjustable soft palate support of the present invention after being assembled.

The combined-type support of the present invention that is implanted in stages may be designed to be combined through convex-concave engagement (see FIG. 26 to FIG. 27) or fastener connection (see FIG. 28 and FIG. 29).

In the combined-type adjustable soft palate support of the present invention, the adjustment mechanism 12 on the hard palate connecting end 1 includes the connecting structure that can be engaged with the near end of the support 2, so that the support 2 may be conveniently fixed to the hard palate connecting end 1. See FIG. 26 to FIG. 27.

In addition, in the combined-type adjustable soft palate support of the present invention, the adjustment mechanism 12 of the hard palate connecting end 1 includes a mechanism that is connected to the near end of the support 2 through a fastener. The adopted fastener is usually a titanium screw, rivet, or positioning block. See FIG. 28 and FIG. 29.

Further, in order to improve the rigidity of the support 2, the flat support 2 may be configured to have an arc-shaped or corrugated cross section, or a common method of increasing the rigidity of the flat object by using reinforcing ribs or the like is adopted.

Embodiment 9

A Soft Palate Support of the Present Invention with an Arc-Shaped Cross Section

Referring to FIG. 30 and FIG. 31, the difference of this embodiment lies in that, the cross section of the support 2 is arc-shaped. The support 2 with the arc-shaped cross section has an advantage of good rigidity. For the supports 2 manufactured from titanium metal plates of the same material and thickness by the same process, the support 2 with the arc-shaped cross section has better rigidity than that with a rectangular cross section.

Figures 34, 35:
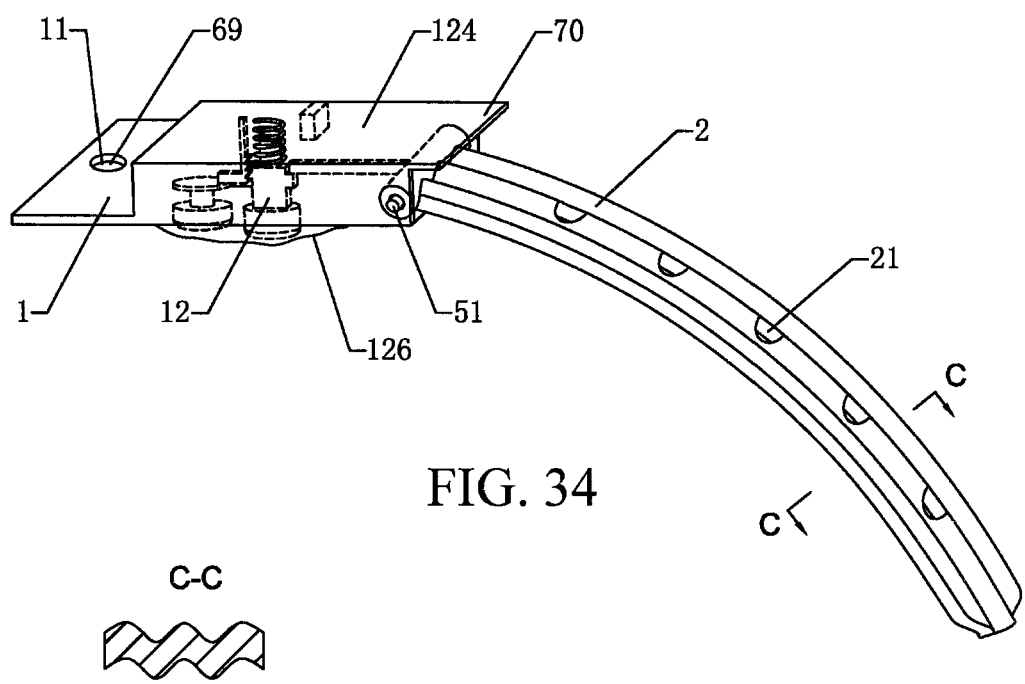
FIG. 34 is a schematic structural view of an adjustable soft palate support of the present invention, in which in this embodiment, the cross section of the support 2 is corrugated, and the support 2 has good rigidity.
FIG. 35 is a B-B cross-sectional view of FIG. 34.

In addition, many methods may be adopted for improving the rigidity of the flat object, for example, a reinforcing rib is configured at the back of the support 2, which may improve the rigidity of the support 2, see FIG. 32 and FIG. 33; or, the support 2 is stamped into a corrugated shape or a wave shape, which also may improve the rigidity of the support 2, see FIG. 34 and FIG. 35.

It should be noted that, the structures disclosed and described in the present invention may be replaced by other structure with the same effect, and the embodiments described in the present invention are not intended to limit the present invention. Though the preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

What is claimed is:

1. An adjustable soft palate support, being a flat implant made of materials capable of being implanted into a human body for a long term, comprising:
    a flat implant support capable of being inserted into a soft palate; and
    a hard palate connecting end, configured to connect the flat implant support to a hard palate,
    wherein the hard palate connecting end comprises:
    a connecting structure, configured to fix the hard palate connecting end to the hard palate; and
    an adjustment mechanism on the hard palate connecting end, configured to control a movement or a curvature of the flat implant support,
    wherein the adjustment mechanism comprises:
        a switch structure having an on state and an off state, wherein
        when the adjustment mechanism is in the on state, the flat implant support implanted into the soft palate is capable of moving with a natural swinging of the soft palate;
        when the adjustment mechanism is in the off state, the flat implant support implanted into the soft palate is capable of lifting the soft palate towards a tongue root and changing a central axis of the soft palate during the natural swinging, so as to enlarge an airway of a pharynx during breathing, and
        the switch structure further comprises one selected from the group consisting of a spring pushrod-type switch structure and a double-button type switch structure.

2. The adjustable soft palate support according to claim 1, wherein the adjustment mechanism (12) on the hard palate connecting end (1) comprises: an adjustment control key (125) mounted on a housing (124), and the adjustment control key (125) is covered by a flexible polymer material film (126) capable of being implanted into the human body.

3. The adjustable soft palate support according to claim 2, wherein the housing (124) includes the flexible polymer material film (126) capable of being implanted into the human body, and the adjustment control key (125) is covered by the flexible polymer material film (126).

4. The adjustable soft palate support according to claim 1, wherein the flat implant support has a radian matching a natural curvature of the soft palate when the soft palate of the human body relaxes.

5. The adjustable soft palate support according to claim 1, wherein the connecting structure on the hard palate connecting end comprises one of a group of structures consisting of: a hole structure, a U-shaped clamp structure, a hook structure, a rivet-type structure, and a self-expanding lock structure.

6. The adjustable soft palate support according to claim 1, wherein the hard palate connecting end (1) further comprises: a housing (124), and the adjustment mechanism (12) is mounted inside the housing (124).

7. The adjustable soft palate support according to claim 1, wherein the flat implant support is a flat object having zero or more holes.

8. The adjustable soft palate support according to claim 1, wherein the flat implant support is selected from the group of structures consisting of: a flat object having an arc-shaped cross section, a flat object having a corrugated cross section, and a flat object having reinforcing ribs.

9. The adjustable soft palate support according to claim 1, wherein the flat implant support is integrally or detachably connected to the hard palate connecting end.

10. The adjustable soft palate support according to claim 1, wherein the flat implant support is inserted into the soft palate by a length equal to $1/5$ to $4/5$ of a total length of the soft palate.

* * * * *